US009225943B2

(12) United States Patent
Li et al.

(10) Patent No.: US 9,225,943 B2
(45) Date of Patent: Dec. 29, 2015

(54) PTZ VIDEO VISIBILITY DETECTION METHOD BASED ON LUMINANCE CHARACTERISTIC

(75) Inventors: Bo Li, Nanjing (CN); Jian Yu, Nanjing (CN); Xiao Zhang, Nanjing (CN); Rong Dong, Nanjing (CN); Dengbiao Jiang, Nanjing (CN); Zhaozheng Chen, Nanjing (CN); Qimei Chen, Nanjing (CN)

(73) Assignee: Nanjing University, Nanjing (CN)

( * ) Notice: Subject to any disclaimer, the term of this patent is extended or adjusted under 35 U.S.C. 154(b) by 363 days.

(21) Appl. No.: 13/981,163

(22) PCT Filed: Aug. 11, 2011

(86) PCT No.: PCT/CN2011/078247
§ 371 (c)(1),
(2), (4) Date: Aug. 15, 2013

(87) PCT Pub. No.: WO2012/100522
PCT Pub. Date: Aug. 2, 2012

(65) Prior Publication Data
US 2013/0342692 A1      Dec. 26, 2013

(30) Foreign Application Priority Data
Jan. 26, 2011  (CN) .......................... 2011 1 0028103

(51) Int. Cl.
*H04N 7/00*    (2011.01)
*H04N 7/18*    (2006.01)
(Continued)

(52) U.S. Cl.
CPC ............... *H04N 7/18* (2013.01); *G01N 21/538* (2013.01); *G06T 7/00* (2013.01); *G06T 2207/10016* (2013.01); *G06T 2207/30252* (2013.01)

(58) Field of Classification Search
CPC ...................................... H04N 7/18
USPC ........................................ 348/143
See application file for complete search history.

(56) References Cited

U.S. PATENT DOCUMENTS 3,501,239 A    3/1970  Rouet

FOREIGN PATENT DOCUMENTS

CN         101382497 A  *  3/2009

OTHER PUBLICATIONS

Li, Bo et al Visibility Detection Based on Traffic Video Contrast Analysis without Artificial Markers, Journal of computer-aided design & computer graphics, vol. 21, No. 11, pp. 1575-1582.
(Continued)

*Primary Examiner* — Sath V Perungavoor
*Assistant Examiner* — Jeffery Williams
(74) *Attorney, Agent, or Firm* — Tresure IP Group, LLC

(57) ABSTRACT

Disclosed is a PTZ video visibility detection method based on luminance characteristic, which includes acquiring a road condition video image by utilizing a PTZ video camera, extracting the region of interest ROI of the road surface to obtain high constancy of selected pixels; acquiring precise road surface region by utilizing region-growing algorism based on Nagao filtering to ensure the illuminance constancy of the selected pixels in world coordinates; in the road surface region, extracting the contrast curve which reflects the luminance variation of the road surface, and searching the feature points of the luminance curve to calculate the human eye distinguishable and maximum far pixels in the image with an extinction coefficient; calculating the maximum visibility distance in combination with camera calibration to determine the visibility value. The present invention can take full advantage of existing PTZ camera to video the road condition and acquire the image without the need of providing any artificial marker. Monitoring can be in real time and has a low monitoring cost, and the monitoring requirement of large area road condition can be satisfied. Monitoring is stable and can not be disturbed by environment. It is a visibility detecting method with the advantages of simpleness, easy realization, high precision and excellent use effect.

7 Claims, 5 Drawing Sheets

Flowchart of the invention

(51) Int. Cl.
    *G01N 21/53*    (2006.01)
    *G06T 7/00*    (2006.01)

(56) References Cited

OTHER PUBLICATIONS

Chen, Zhaozheng et al Video Contrast Visibility Detection Algorithm and Its Implementation Based on Camera Self-calibration, Journal of Electronics & Information Technology, Dec. 2010, vol. 32, No. 12, pp. 2907-2912.
An, Mingwei et al Visibility detection method and system design based on traffic video, Chinese oumal of Scientific Instrument, May 2010, vol. 31, No. 5, pp. 1148-1153.
T. M. Kwon. Atmospheric visibility measurements using video cameras: Relative visibility. Technical report[R], America: University of Minnesota Duluth, Jul. 2004.
Robert G. Hallowell, Michael P. Matthews, and Paul A. Pisano, Automated Extraction of Weather Variables from Camera Imagery [C]. Proceedings of the 2005 Mid-Continent Transportation Research Symposium, Ames, IA, Aug. 2005.
Final Report on Signal and Image Processing for Road Condition Classfication [R], AerotechTelub and Dalarma University under the7 Swedish National Road Agency. Report #Feb. 6, 2002. Jul. 2002.
Chen Zhaozheng, Zhou Qingkui, Chen Qimei, Video visibility detection algorithm based on wavelet transformation, Chinese Journal of Scientific Instrument, vol. 31 No. 1, Jan. 2010.
Graphical Noise reduction based on SPCNN and Nagao wave, 2009, 39(6): 598-607.
Li Bo, Chen Qimei. Vehicle activity analysis from freeway traffic video [J]. Chinese Journal of Scientific Instrument, 2006,27(Suppl. 3): 2118-2120.
Yu Lina, Hu Zheng-ping, Lian Qiu-sheng, Hybrid Circle and Ellipse Fast Detection Using Improved Randomized Hough Transform,Journal of El ectronic Measurement and Instrument, 2004, 18 (2) : 92 97.
Jiang Lian-yuan, Fast detection of multi-circle with randomized Hough transform, Optoelectronics Letters, vol. 5 No. 5, Sep. 1, 2009.
First office action for Chinese counterpart application 201110028103.5, dated Feb. 28, 2012.

* cited by examiner

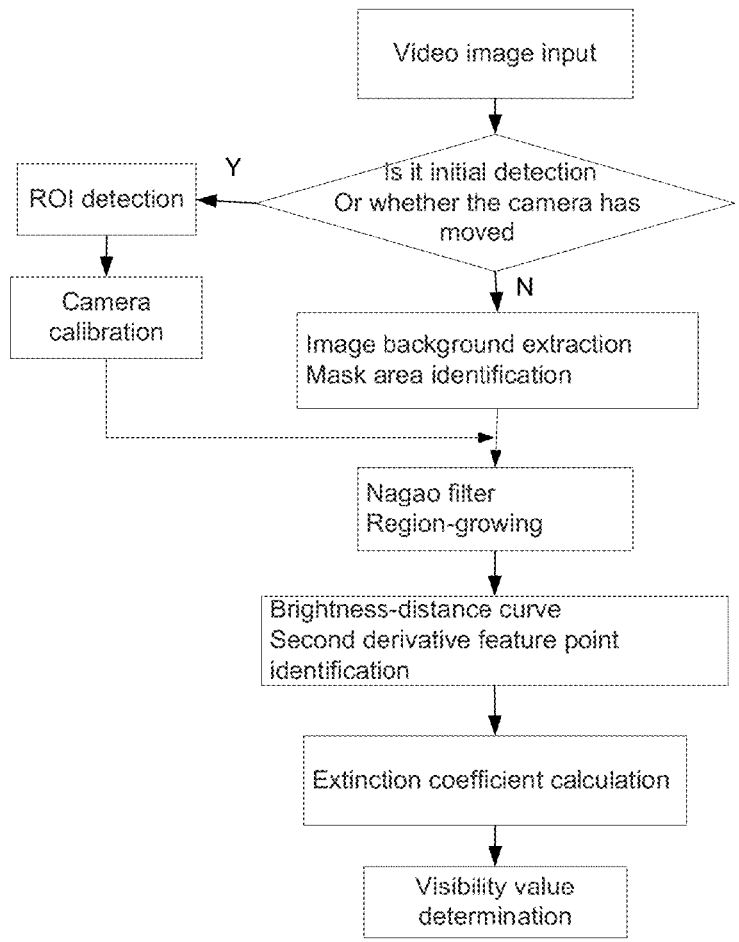
Figure 1. Flowchart of the invention
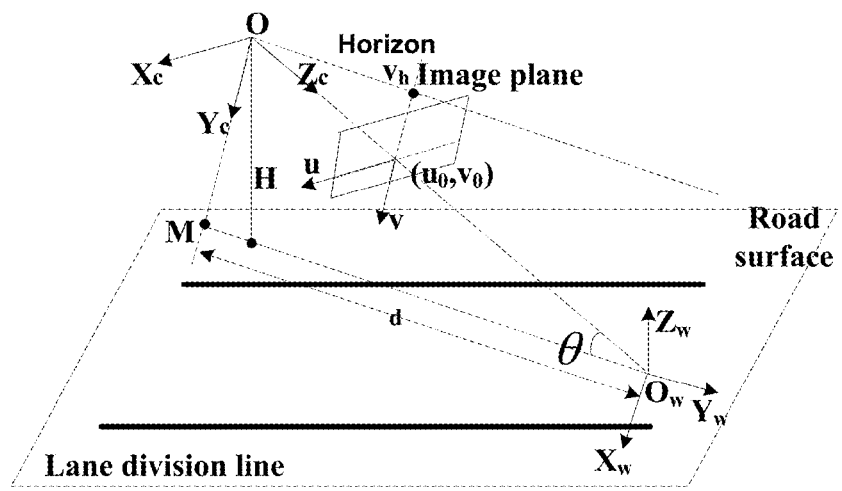
Figure 2. Camera calibration model diagram

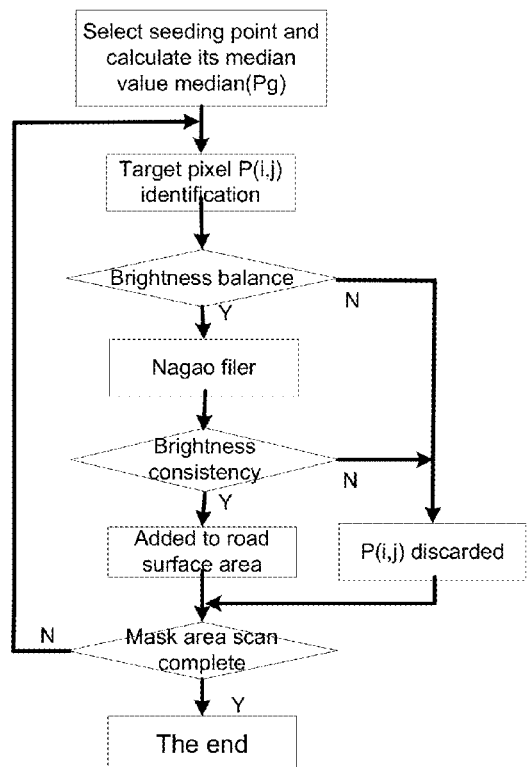
Figure 3. Flowchart of the invention to ensure the consistency of brightness using the region-growing method
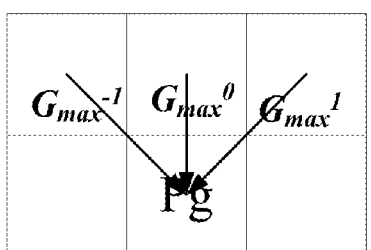
Figure 4. Schematic diagram of the region-growing algorithm using top 3-neighborhood seeding

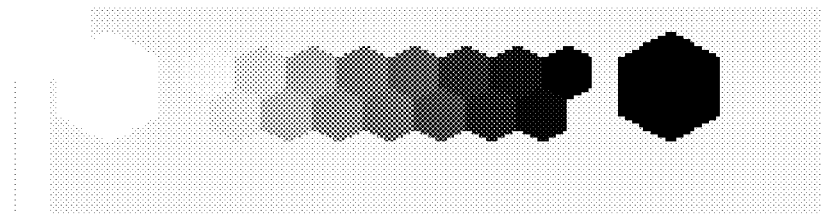
Figure 5. A gray scale image corresponding to step 6) of the visibility calculation
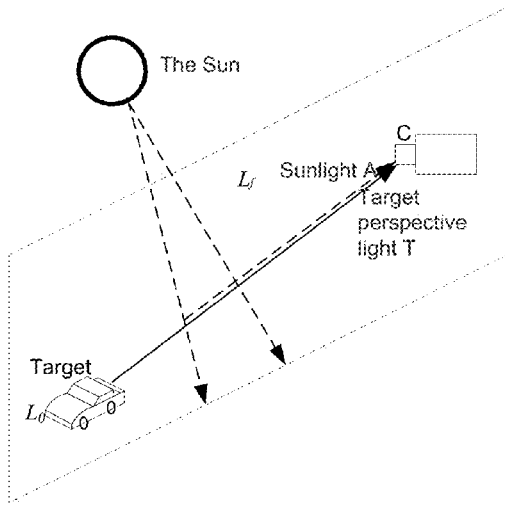
Figure 6. Schematic of the actual brightness of the target composition measured by the camera
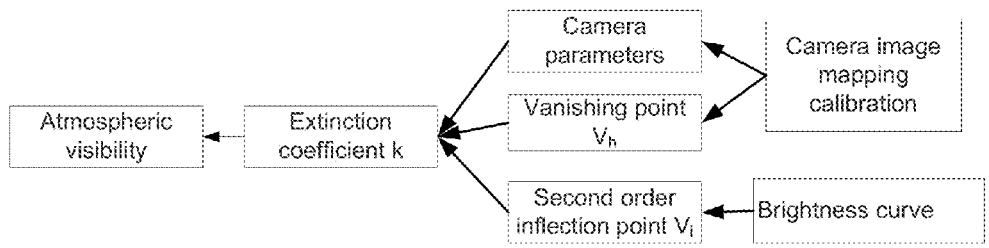
Figure 7. Flowchart of the visibility solution process based on brightness feature point

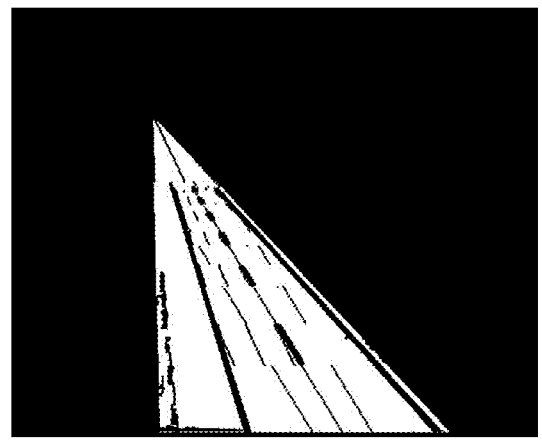
Figure 8. Schematic of the pretreated road surface measuring band
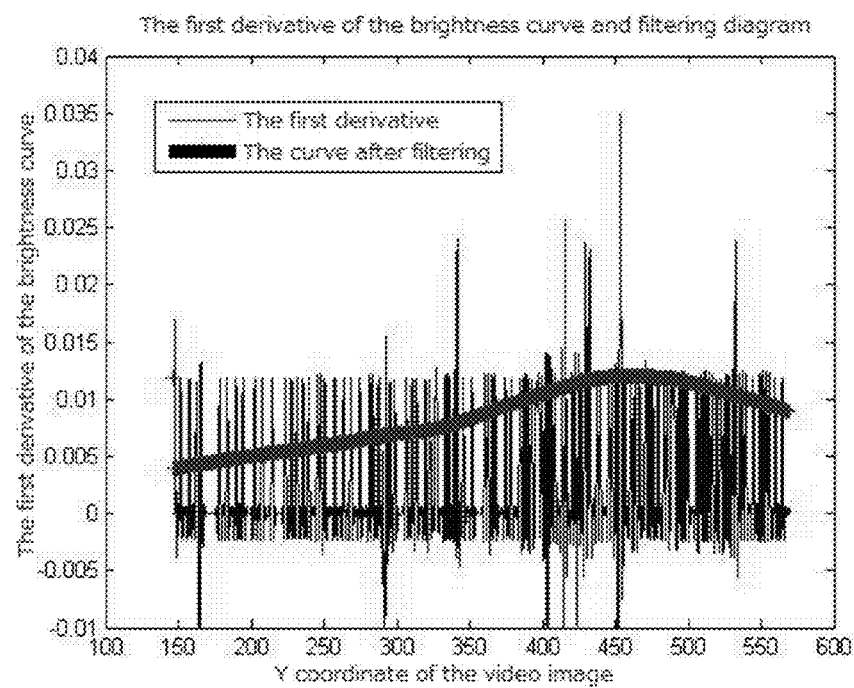
Figure 9. A diagram of the first derivative of the luminance variation curve and filtering diagram

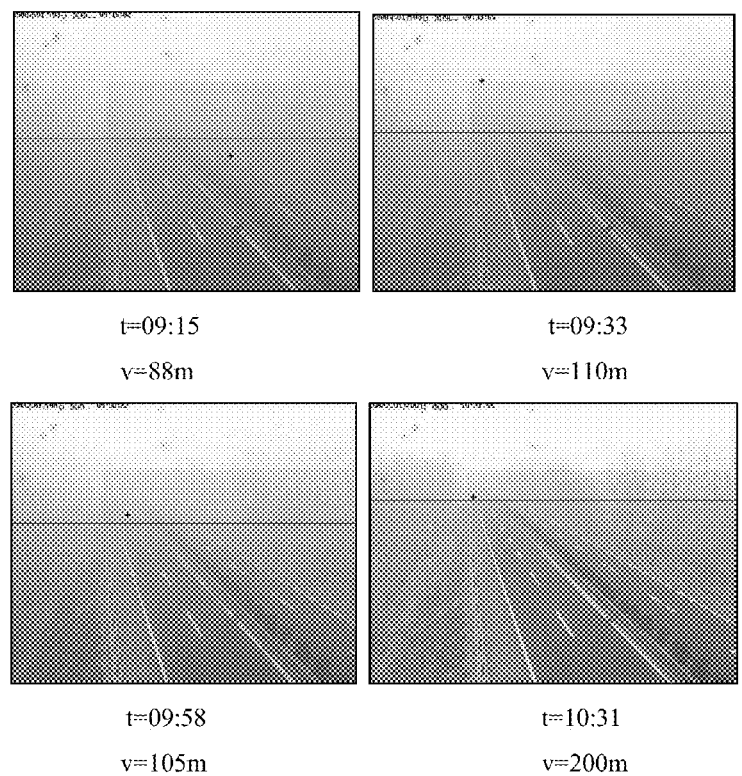
Figure 10. Actual testing results of the invention
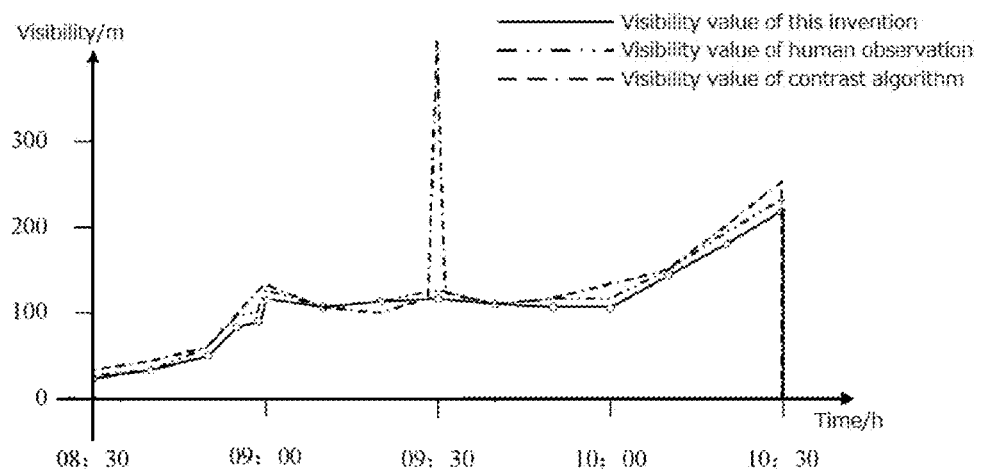
Figure 11. A comparison of the actual testing results, contrast algorithm, and human eye observation

US 9,225,943 B2

PTZ VIDEO VISIBILITY DETECTION METHOD BASED ON LUMINANCE CHARACTERISTIC

CROSS REFERENCE TO RELATED APPLICATION

This application is a National Phase application of, and claims priority to, PCT Application No. PCT/CN2011/078247, filed on Aug. 11, 2011, entitled "PTZ VIDEO VISIBILITY DETECTION METHOD BASED ON LUMINANCE CHARACTERISTIC", which claimed priority to Chinese Application No. 201110028103.5, filed on Jan. 26, 2011. Both the PCT Application and Chinese Application are incorporated herein by reference in their entireties.

TECHNICAL FIELD

This invention belongs to the field of image processing technology. It involves camera calibration technology utilizing adaptive Nagao filter technology, noise suppression technology, and visibility solution technology. Under the assurance of consistent height and illumination of the selected pixels, this method extracts the contrast curve reflecting the actual changes of road surface brightness variation, searches for the feature point of the brightness curve, and calculates the farthest pixel in the image which are distinguishable by human eye through the use of extinction coefficient; combined with camera calibration, this method determines maximum visibility distance and identifies the visibility value. Specifically, this is a PTZ video visibility detection method based on image luminance characteristics.

BACKGROUND

Highway system involves itself in national economy and is an emerging industry in China. By 2010, China's total highway mileage will exceed 80,000 km. Jiangsu Province is China's economically developed region and is currently a leader of the country's Intelligent Transportation System (ITS). Jiangsu has 3,558 km of existing expressways with a highway density of 3.46 km/100 square km. By the end of 2010, its total highway mileage is projected to reach 5,000 kilometers.

China's landscape extends from plains, rivers, and lakes to other land systems. In the middle and western regions of China, the topography of hills and terrains is complex and disastrous weather conditions such as fog, haze are frequent occurrences. These hazardous weather conditions occurring at uncertain times and places create great risks to highway transportation, especially to vehicle safety concerns. In 1975, highways from California to New York in the United States resulted in more than 300 vehicles collisions and killing more than 1,000 people because of heavy fogs and these are considered to be the world's most serious traffic accidents. 1986 in France alone, there were 1,200 accidents (excluding urban areas) attributed to fogs, causing 182 dead and 175 injuries, with 1,352 people slightly injured. Although accident rate due to fog on highways is 4% annually, the mortality rate is as high as 7% to 8%. In terms of measurement and management, the Shanghai-Nanjing Expressway has about 10 meteorological observation stations for a cost of nearly ten million. It is still difficult to accurately detect the occurrence of fog in certain areas.

To deal with the low visibility problem, China's highway management departments initiate road closures to reduce traffic accidents. Because of the subjectivity and lack of quantitative indicators, the implementation of traffic control and management procedures are not scientific and not sufficiently standardized to be efficient, sometimes this procedure of road closures is even counterproductive. To this end, real-time meteorological road condition monitoring, especially timely detection and reporting of low visibility condition is the key to enhance our ability to respond to disastrous weather conditions, to reduce losses and to improve highway management efficiency.

Currently installed highway meteorological visibility monitoring and testing equipment is mainly conventional laser visibility meter-based, generally available atmospheric transmission analyzer and scattering instrument. These two types of equipment can cause large number of errors in the condition of heavy rain, fog and other low visibility weather due to moisture absorption and difficulty of normal observation. It is difficult to accurately detect the occurrence of fog in certain areas. Additionally, high manufacturing cost and maintenance cost of these meteorological monitoring stations make them hard to be popularized and to be implemented in a wide area. For instance, the 10 or so meteorological monitoring and detection stations along Shanghai-Nanjing Expressway cost nearly ten million.

Video visibility detection technology utilizes video image analysis and artificial intelligence, combined with traditional atmospheric optical analysis, to analyze and process video images to establish the relationship between images and the real-time weather condition. Meteorological visibility values are calculated by measuring the changes of image characteristics. Compared with traditional methods, this detection method basically resembles human eyes in viewing objects. This technology possesses the characteristics of low-cost, easy of operation, and compatibility with the cameras already operating along the roadsides, which has the advantages of existing wide area coverage. However, this is a new technology and needs improvement.

At present, there are very few studies being conducted outside of China. Most of them are still in the theoretical development and experimental stage. University of Minnesota in the United States proposed a video visibility detection method using fixed distance from the target object[1]. The need of artificially preset multiple video detection targets, high cost, complicated operation, vulnerability to the effects from terrain and other environmental factors are all limitations of this method. A team from MIT put forward a method to calculate relative visibility based on logo images[2]. This method obtains relative visibility by comparing the detected scene images to pre-stored images of known meteorological visibility. This method does not need auxiliary facilities and is easy to use. But it is difficult to use this method with PTZ cameras and it is susceptible to interferences from moving objects. Swedish National Road Administration Center had proposed a visibility detection method based on neural network and infrared video imaging[3]. This method extracts visibility reading from different edges of the images, classifies them using neural network algorithm, and converts the results to corresponding visibility levels. These infrared cameras have relatively low operating noise but they are expensive and complex to maintain, therefore it is difficult to install these infrared cameras in a reasonable density along the road.

Reference [4] proposed a visibility detection method based on the visibility of road markers. This method uses a detecting and matching algorithm with image segments from a preset target to obtain its characteristics and arrives at corresponding visibility values. This method requires the installation of additional markers and resulting in higher cost. In addition, the detection range and accuracy of this method is limited by the field of view and the distance and number of the targets. It is also difficult to retrofit existing PTZ cameras to be compatible with this method. Reference [5] talked about a detection method based on video image contrast analysis. By analyzing and contrasting each pixel and its neighboring pixels, a condition of the selected maximum value larger than a given threshold value indicates a human eye distinguishable image. Combined with the camera calibration, a visibility value is calculated. Because of the threshold value division, this method is susceptible to noise, including the lane division line area noise and CCD imaging current noise. In particular, quantification error and noise of the procedure can lead to hopping results and the algorithm is not stable enough.

REFERENCES

[1] T. M. Kwon. Atmospheric visibility measurements using video cameras: Relative visibility. Technical report[R], America: University of Minnesota Duluth, July 2004.

[2] Robert G. Hallowell, Michael P. Matthews, and Paul A. Pisano, Automated Extraction of Weather Variables from Camera Imagery[C]. Proceedings of the 2005 Mid-Continent Transportation Research Symposium, Ames, Iowa, 2005.8

[3] Final Report on Signal and Image Processing for Road Condition Classification[R], AerotechTelub and Dalarma University under the7 Swedish National Road Agency. Report #2002-02-06. 2002.6.

[4] Chen Zhaozheng, Zhou Qingkui, and Chen Qimei, Visibility Detection Algorithm and Implementation Based on Transformation of Wavelet[J]. Journal of Scientific Instruments 2010, 31 (1): 92~98

[5] Li Bo, Dong Rong, and Chen Qimei, Road Visibility Detection Using Video Contrast without Artificial Markers [J]. Journal of Computer Aided Design and Imaging, 2009, 11 (21):1575-1982

[6] Li Bo, Chen Qimei. Vehicle activity analysis from freeway traffic video[J]. Chinese Journal of Scientific Instrument, 2006, 27(Suppl.3): 2118-2120 (in Chinese)

[7] Yu Lina, Hu Zhengping, and Lian Qiusheng, Rapid Detection Method Based on Improved Hough Transform with Random Mix of Circles and Ovals[J]. Journal of Electronic Measurement and Instrument, 2004, 18 (2): 92~97

[8] Jiang Lianyuan, Fast Detection of Multi-circle with Randomized Hough Transform[J]. Optoelectronics Letters VOL5, 2009

[9] Zhang Yudong, Wu Lenan, De-noising Using SPCNN and Nagao Filtering, Chinese Science Series F: Information Science, 2009, 39 (6): 598-607

[10] Nagao M, Takashi M. Edge preserving smoothing. Comput Graph Image Process, 1979, (9): 394-407

SUMMARY OF THE INVENTION

The problem to be solved by this invention is described as follows: The shortcomings of existing visibility detection and monitoring technology includes very limited detection area, difficulty in meeting the needs of monitoring large area road condition, lack of real-time monitoring and reporting, high o perating cost, and high susceptibility of monitoring accuracy, etc. We are in need of a simple and easily implemented visibility detection and monitoring method which is accurate and efficient.

The technical proposal of this invention is as follows: This is a visibility detection method based on the image luminance characteristics of PTZ video images. This method acquires road condition video images by using PTZ video cameras, extracts the region of interest (ROI) of road surface, and achieves high level of consistency in the height of selected pixels. This method utilizes an accurate road surface area obtained with a region-growing algorithm based on Nagao filter to eliminate interferences from roadbed and vehicles, and ensures consistent level of illumination for the selected pixels on the world coordinates. Within the road surface area, this method extracts the contrast curve reflecting actual changes of road surface brightness variation, searches for the feature point of the brightness curve, and calculates the farthest image pixel distinguishable to human eyes through the use of extinction coefficient; it calculates the maximum visibility distance and derives visibility value in combination with camera calibration. This procedure consists of the following steps:

1) Real-time video traffic images are acquired using existing PTZ cameras;
2) After processing the images from the video cameras, the transformation relationship between the images and their corresponding world coordinates of road surface is determined through the camera calibration technology and the distances between the images of the road surface and cameras are calculated;
3) Using Kluge model fitting lane division lines to the projections of the video images, through the unknown parameters from randomly solved Hough model, the area between the lane division lines is designated as current region of interest (ROI); subsequent imaging processing are limited within ROI to ensure the consistency of image pixel heights;
4) Using region-growing algorithm, combined with ROI brightness criteria and adaptive Nagao filtering method, road mask area is accurately extracted and all subsequent processing are focused on the mask area to reduce the number of calculations and to ensure consistent brightness of the selected pixels within the world coordinates: to calculate the gray scale median value median $(P_g)$ of the bottom-most line of the ROI, the pixel with brightness of median$(P_g)$ is selected as seeding point, mask area is then scanned according to bottom-to-top, left-to-right progressive scan principle, scanned target pixel $P(i, j)$ is in turn determined whether it belongs to the road surface area according to the following growth criteria:

41) Brightness balance
$P(i, j)$ and median$(P_g)$ satisfy $$P(i,j) - \text{median}(P_g) \leq \rho n_r \min G_{max}^k$$
$$(k=-1,0,1) \hspace{2cm} (6)$$

In formula (6), $\rho$ is a constant less than 1, $n_r$ is the number of separating rows between $P(i, j)$ and initial seeding point $P_g$, $G_{max}$ refers to the brightness difference between the pixel and its top 3-neighborhood pixels, i.e. top-left, top, and top-right, with top-left brightness difference as $G_{max}^{-1}$, top brightness difference as $G_{max}^{0}$, and top-right brightness difference as $G_{max}^{1}$, among them:

$$G_{max}^{-1} = G_{max}^{1} < G_{max}^{0} \hspace{2cm} (7)$$

42) Illumination consistency

With image noise filtered using adaptive window width Nagao median filter without diffusing noise point energy, the pixels meeting the balance of pixel brightness are further filtered with adaptive window width Nagao median filter to get the pixel gray scale value $Q(i, j)$ which satisfies:

$$\exists m \in \{i-1, i, i+1\}$$
$$Q(i,j) - Q(m,j+1) < G_{max}^{i-m} \hspace{2cm} (8)$$

Pixels meeting the continuity and consistency of brightness are added to the road surface domain until the mask area scan is complete, resulted in an accurate road surface area;

5) Extraction of brightness feature: using the initial road surface domain with consistent illumination and consistent pixel height obtained in the previous step, coupled with the analysis on the trend of change in road surface pixel luminance caused by atmospheric extinction, feature point of change is identified, which is also the zero point for the second derivative of the luminance curve;

6) Visibility calculation: using the vanishing point coordinates obtained through camera calibration algorithm and the camera parameters, together with the zero point coordinates from the second derivative of luminance curve, atmospheric extinction coefficient is determined; the Koschmieder Theory is then used to deduce the relationship between atmospheric extinction coefficient and visibility, thus resulting in the visibility value.

Camera calibration process as described in step 2):

PTZ video camera image mapping model includes three coordinate systems: road surface world coordinate system $(X_w, Y_w, Z_w)$, the camera coordinate system $(X_c, Y_c, Z_c)$, and the video image on the image plane coordinate $(u,v)$; with the angle between $Z_c$ and road surface as $\theta$, the distance from camera optical center O to road surface as H, and f as the effective focal length of the lens, the transformation relations between the road coordinate system and the camera coordinate system, the camera coordinate and the image plane are as follows:

$$\begin{pmatrix} X_c \\ Y_c \\ Z_c \\ 1 \end{pmatrix} = \begin{pmatrix} 1 & 0 & 0 & 0 \\ 0 & -\sin\theta & -\cos\theta & H\cos\theta \\ 0 & \cos\theta & -\sin\theta & H\sin\theta \\ 0 & 0 & 0 & 1 \end{pmatrix} \begin{pmatrix} X_w \\ Y_w \\ Z_w \\ 1 \end{pmatrix} \quad (1)$$

$$u = -f\frac{X_c}{Z_c} \quad v = -f\frac{Y_c}{Z_c} \quad (2)$$

With $Y_w = +\infty$ we get the horizon $v_h$, which is the vanishing point in the image plane of the projection:

$$v_h = -f\tan\theta \quad (3)$$

Put this in formula (2) we have:

$$\frac{v - v_h}{f} = \frac{Y_c}{Z_c} + \tan\theta \quad (4)$$

$$Y_c = L - d\sin\theta \quad Z_c = d\cos\theta$$

Accordingly, the distance between the pixels in an image area representing road surface and the camera optical center $d_c$ can be expressed as:

$$d_c = \begin{cases} \dfrac{\lambda}{(v - v_h)} & v > v_h \\ \infty & v \leq v_h \end{cases} \quad (5)$$

$$\lambda = \frac{Hf}{\cos^2\theta}$$

The relationship between atmospheric visibility and extinction coefficient in step 6) is:

According to Koschmieder Equation, let atmospheric extinction coefficient be k, an object of fixed brightness at a distance of d from the observing human eye, with the luminance or radiance value of L, the brightness of the object itself $L_0$, and the background luminance $L_f$ have a relationship as described in the following expression:

$$L = L_0 e^{-kd} + L_f(1 - e^{-kd}) \quad (9)$$

Formula (9) indicates that the brightness of an object consists of two parts: intrinsic brightness of the object $L_0$, which weakens at the rate of $e^{-kd}$, and the background luminance $L_f$, which strengthens at the rate of $1-e^{-kd}$, the relationship between the contrast change, the atmospheric extinction coefficient k, and the distance d is as follows:

$$C_d = \frac{L - L_f}{L_f} = \frac{L_0 - L_f}{L_f} e^{-kd} = C_0 e^{-kd} \quad (10)$$

In formula (10), $C_d$ is the receiving brightness contrast of the target object, and $C_0$ is the intrinsic brightness contrast; the relationship expressed in formula (10) is true when the scattering coefficient is independent of the azimuth angle and there is a uniform illumination along the whole path along the observer, the object, and the horizon sky.

Let $V_{met}$ be the maximum distance of observation by human eyes, i.e. the pixel points with a contrast ratio of 0.05, we have:

$$V_{met} = -\frac{1}{k}\ln\left(\frac{C_d}{C_0}\right) = -\frac{1}{k}\ln(0.05) \approx \frac{3}{k} \quad (11)$$

Equation (11) expresses the relationship between the atmospheric visibility and the extinction coefficient;

The solution process for visibility value based on luminance characteristic point is as follows:

Seeking the second derivative of the image brightness curve L in relation to vertical coordinate v of image plane, substituting distance d with equation (5), we have:

$$\frac{d^2L}{dv^2} = k\frac{\lambda(L_0 - L_f)}{(v - v_h)^3} e^{-k\frac{\lambda}{v - v_h}}\left(\frac{k\lambda}{v - v_h} - 2\right) \quad (12)$$

Under the effect of the extinction coefficient k, the image pixel brightness L and its derivative change with distance; as the fog becomes denser, the target object becomes more blurred with the sky as background, and the extreme point value is decreasing; let the second derivative be 0 and discard the meaningless solution when k=0, we get:

$$k = \frac{2(v_i - v_h)}{\lambda} \quad (13)$$

Where $v_i$ is the inflection point of the second order luminance curve, i.e. the second derivative zero point, $v_h$ is the horizon or extinction point, whereby the value of atmospheric visibility distance:

$$V_{met} \approx \frac{3}{k} = \frac{3\lambda}{2(v_i - v_h)} \quad (14)$$

As $v_i$ approaches $v_h$, $V_{met}$ is in a critical state, this is the point of time when one can see the fog appearing; when $v_i$ is greater than $v_h$, it is possible to detect the resulting fog; on the other hand, when $v_i$ is less than $v_h$, we consider it as no fog.

The specifics of step 5): within the road surface area obtained in step 4), we in turn search for the maximum length of the continuous set of pixels Pix(i, j) in $j^{th}$ row, which starts at (a, j) and ends at (b, j) with a length of lengh(j)=(b−a+1); the middle point of Pix(i, j) is ((b+a)/2, j), and the midpoint of each line is the center of road surface measuring band; a road surface measuring band is identified under the condition set forth by formula (15):

$$\text{len}(Pix(j)) = \min(\text{Lengh}, \text{lengh}(j)) \quad (15)$$

Where Pix(i) is the set of pixels in $j^{th}$ row of the measuring band, len(Pix(j)) is its length, and Lengh is a constant set threshold; after acquiring the median luminance values in each row of the measuring band, a luminance-distance change curve B is generated; after seeking the second derivative of curve B, the variation feature point $v_i$ is identified which is also the second derivative zero point; to reduce error and get accurate measurements, we interpolate curve B and filter noise to eliminate confusion on the second derivative zero point before we look for the second derivative zero point.

This invention has the following advantages:
1. No need of any artificial markers; make full use of the existing road PTZ cameras to obtain images and to do real-time monitoring; low operation cost;
2. The detection method in this invention has high degree stability; can better adapt to different weather conditions; can accurately determine the extent of fog and haze; and has a detection precision of within 10 meters;
3. This invention uses Nagao window width adaptive median filter, instead of the traditional mean filtering, to ensure the quality of image resolution and the edge effect, and has a better robustness even when the noise density changes widely;
4. This invention achieves a seamless full road visibility detection, including localized fog detection and full road visibility distribution; it provides fog and haze advices regarding safe vehicle speed and possible detour routes, rather than blindly initiates road closures; it provides accurate data to support and improve the utilization of the road and will have important economic benefits.

DESCRIPTION OF THE DRAWINGS

FIG. 1 is the flowchart of the invention.
FIG. 2 is the invention's camera calibration model diagram.
FIG. 3 is the flowchart of the invention to ensure the consistency of brightness using the region-growing method.
FIG. 4 is a schematic diagram of the region-growing algorithm using top 3-neighborhood seeding.
FIG. 5 is a diagram of gray scale image, corresponding to step 6) of the visibility calculation.
FIG. 6 is a schematic of the actual brightness of the target composition measured by the camera.
FIG. 7 is the flowchart of the visibility solution process based on brightness feature point.
FIG. 8 is a schematic of the pretreated road surface measuring band.
FIG. 9 is a diagram of the first derivative of the luminance variation curve and filtering diagram.
FIG. 10 shows actual testing results of the invention.
FIG. 11 shows a comparison of the actual testing results, contrast algorithm, and human eye observation.

DETAIL DESCRIPTION of SELECTED EXAMPLES

This invention uses digital cameras to simulate the analog perceptual characteristics of the human eyes. Through the study of contrast in video image pixels and brightness change trend, image features are transformed into intensity level of human perception, thus resulting in the visibility value. Instead of deploying humans to watch monitoring videos provided by elaborated equipment setup in order to collect complex field data and traffic parameters, this invention proposes a unified video processing method. This invention utilizes existing highway surveillance camera system, which currently provides wide-area coverage and direct video feeds, to collect and process road conditions and provide visibility information as a result. This invention has the advantages of wide-area coverage, low cost, low false alarm rate, low missing rate, and high precision detection rate. This invention provides a real-time traffic monitoring and information collection system with high coverage density, low cost, and easy to maintain.

As illustrated in FIG. 1, this invention uses PTZ video cameras to obtain traffic video images and road conditions, extracts the region of interest (ROI) of road surface, and achieves the consistency of selected image pixel height; this invention utilizes an accurate road surface area obtained with region-growing algorithm based on Nagao filter to eliminate interferences from roadbed and vehicles, and ensures consistent level of illumination for the selected pixels on the world coordinates; within the road surface area, this invention extracts the contrast curve reflecting actual changes of road surface brightness variation, searches for the feature point of the brightness curve, and calculates the farthest image pixel distinguishable to human eyes through the use of extinction coefficient; it determines the maximum visibility distance and derives visibility value in combination with camera calibration. This invention uses PTZ video cameras, namely Pan, Tilt, and Zoom features, to horizontally and vertically change viewing angle and zoom cameras to monitor the environment.

This invention includes the following steps:
1) Using existing PTZ video cameras to collect real-time video images and obtain traffic and road condition information;
2) After processing the images from the video cameras, the transformation relationship between the images and their world coordinates of road surface are determined through the camera calibration technology and the distances between road surface area of the images and cameras are calculated;
3) Using Kluge model fitting lane division lines to the projections of the video images, through the unknown parameters from randomly solved Hough model, the area between the lane division lines is designated as current region of interest (ROI); subsequent imaging processing are limited within ROI to ensure the consistency of image pixel height;
4) With the effect of atmospheric light scattering, the image surface pixel brightness of the road surface shows some variation with regard to distance. The hopping change of the brightness on roadbed and lane dividing lines may also cause large number of errors during the extraction process. This method uses a region-growing algorithm, combined with ROI brightness criteria within the region as well as the adaptive Nagao filtering method, to accurately extract road mask area. All subsequent processing will be limited to the mask area in order to reduce the amount of calculations and to ensure consistent illumination of the selected pixels in the world coordinates. According the principle of camera projection imaging, the bottom few lines of the ROI image will be for the pavement area. Therefore, we calculate the gray median value of the bottom-most line, denoted as median($P_g$), and the pixel with a brightness of median($P_g$) is selected as seeding pixel. The mask area is scanned with bottom-to-top, left-to-right principle of progressive scan. The resulting target pixels P(i,j) is in turn determined if it belongs to the road surface area according the following growth principle: pixels meet brightness continuity and consistency are added to the road surface area. This process continues until the whole mask area is scanned and an accurate road surface area is obtained;

5) Brightness feature extraction: Using the initially obtained road surface area with consistent luminance feature and consistent pixel height, pixel luminance change trend due to atmospheric extinction is identified as the variation point, this is also the second derivative zero point of the luminance curve;

6) Visibility calculation: As illustrated in FIG. 7, using the vanishing point coordinates derived from the camera calibration algorithm and camera parameters, together with the zero point coordinates of the second derivative of the brightness curve, the atmospheric extinction coefficient is calculated; the Koschmieder Theory is subsequently used to deduce the relationship between atmospheric extinction coefficient and visibility; the visibility value is eventually determined.

This invention further assumes the brightness of the image changes gradually with distance. Because the brightness values are discrete integer values from 0 to 255, sometimes adjacent rows of pixels will have the same brightness value as a result. Furthermore, many confusing second derivative zero point values could exist due to interferences from noise points. In order to avoid false detection, luminance curve interpolation and filtering techniques are used to eliminate confusing second derivative zero points before we look for the point of mutation.

The PTZ camera image mapping calibration module mentioned in step 2) is calculated as follows:

According to the traffic camera image mapping model, as shown in FIG. 2 and described in detail in reference [8], there are three coordinate systems. They are the road coordinate system ($X_w, Y_w, Z_w$), the camera coordinate system ($X_c, Y_c, Z_c$), and the image plane coordinates (u, v). With the angle between $Z_c$ and the road as θ, the distance from camera optical center O to the surface as H, and f as the effective focal length of the lens, the transform relationships between the road coordinate system and camera coordinate system, camera coordinate system and the image plane are established as:

$$\begin{pmatrix} X_c \\ Y_c \\ Z_c \\ 1 \end{pmatrix} = \begin{pmatrix} 1 & 0 & 0 & 0 \\ 0 & -\sin\theta & -\cos\theta & H\cos\theta \\ 0 & \cos\theta & -\sin\theta & H\sin\theta \\ 0 & 0 & 0 & 1 \end{pmatrix} \begin{pmatrix} X_w \\ Y_w \\ Z_w \\ 1 \end{pmatrix} \quad (1)$$

$$u = -f\frac{X_c}{Z_c} \quad v = -f\frac{Y_c}{Z_c} \quad (2)$$

With $Y_w = +\infty$ we get the horizon $v_h$, which is the vanishing point in the image plane of the projection:

$$v_h = -f \tan\theta \quad (3)$$

Put this in formula (2) we have:

$$\frac{v - v_h}{f} = \frac{Y_c}{Z_c} + \tan\theta \quad (4)$$

$$Y_c = L - d\sin\theta \quad Z_c = d\cos\theta$$

Accordingly, the distance between the pixels in an image area representing road surface and the camera optical center $d_c$ can be expressed as:

$$d_c = \begin{cases} \dfrac{\lambda}{(v - v_h)} & v > v_h \\ \infty & v \leq v_h \end{cases} \quad (5)$$

$$\lambda = \frac{Hf}{\cos^2\theta}$$

Step 3) and step 4) ensure video image consistency from the perspectives of pixel height consistency and illumination coherence, respectively.

3) The ROI detection process described in step 3) ensures the consistency of height. During the process of road surface imaging, it is sometimes inevitable to lose object height information because roadside trees are often detected as above the horizon line. This problem often leads to the difficulty in turning the image feature point extracted by the camera calibration algorithm into a specific visibility value. To overcome this problem, this invention utilizes Kluge model to fit lane division lines into the video image projection. Through the use of the unknown parameters in randomized Hough transform (RHT), this method detects the lane division lines in the image projection and the area between the lane division lines is identified as the current ROI of the image. Detailed information about Kluge model and its parameters solutions can be found in reference [6]. We limit the subsequent processes within the ROI to ensure image pixels' height consistency and to reduce the complexity of subsequent calculations.

4) Step 4) sets the bottom of the mask area as seed region. This is to ensure that each seed point gray scale value is as equal to the gray scale value of all the pixels in this row as possible. Based on camera projection imaging principle, the bottom a few lines of the ROI image will be the road surface area. By calculating the gray scale median value of the bottom-most row of the ROI, designated as median($P_g$), pixels with brightness of median($P_g$) are selected as seeds and the mask region is progressively scanned according to bottom-to-top, left-to-right principle. Region-growing flowchart is shown in FIG. 3 and target pixel P(i, j) is in turn judged according to the following growth criteria to determine if it belongs to the road surface area.

41) Brightness balance
P(i, j) and median($P_g$) satisfy $$P(i,j) - \text{median}(P_g) \leq \rho n_r \min G_{max}^k$$

$$(k = -1, 0, 1) \quad (6)$$

In formula (6), ρ is a constant less than 1, $n_r$ is the number of separating rows between P(i, j) and initial seeding point $P_g$, $G_{max}$ refers to the brightness difference between the pixel and its top 3-neighborhood pixels, the top 3-neighborhood pixels refer to top-left, top, and top-right, top-left brightness difference is $G_{max}^{-1}$, top brightness difference is $G_{max}^0$, and top-right brightness difference is $G_{max}^1$, as shown in FIG. 4, the following is generally true:

$$G_{max}^{-1} = G_{max}^1 < G_{max}^0 \quad (7)$$

Brightness balance guarantees the prevention of pixel brightness drift. Assuming the image gray scale value ranging from 0 to 255, threshold between two adjacent rows as 8, if we only restrict adjacent rows without adding this specific restriction, it is possible to have a black spot (with a brightness value of 0) after 32 rows and a white spot (with a brightness value of 255) right next to the black spot in the road surface area at the same time, this is a result of a large drift in the pixel gray scale value relative to the seed point gray scale value.

42) Illumination uniformity based on adaptive window width Nagao median filter

We will not give an elaborated discussion of the Nagao median filter since it is described in detail in references [9] and [10]. The pixels meeting the brightness balance criteria are further filtered with adaptive window width Nagao median filter and have a pixel gray scale value of $Q(i,j)$ which satisfies the following:

$$\exists m \in \{i-1, i, i+1\}$$

$$Q(i,j) - Q(m, j+1) < G_{max}^{i-m} \quad (8)$$

This condition, after the removal of image noises, effectively prevents the occurrence of gray scale value hopping within the range.

The idea behind the Nagao algorithm is: turn a long strip of template once around the center pixel; select the template location with minimum variance; replace the center pixel gray scale value with mean gray scale value of the pixels; repeat the process until the number of changing pixel reaches 0.

The adaptive window width Nagao filter is selected by taking into account the angular resolution, edge retention, and computational accuracy.

Adaptive window width Nagao filter makes angular resolution finer in a homogeneous area with the use of large-scale template; while for the edge region and texture area, a small-scale template should be used to avoid blurry edges and textures. Traditional Nagao filter is not ideal because it uses mean value filter. Noise resistance and filtering ability is stronger when the template uses median value filter instead of mean value filter, enabling it to effectively filter out multiple noise points within the template. Adaptive window width Nagao median filter can effectively filter out noise from the roadbed, green belts, and shadows caused by road noise while preserving the mask edge of the area and textural properties. Pixels satisfy the continuity and consistency of brightness is added to the road surface area until the mask area scan is completed, resulting in the exact road surface area.

The brightness feature extraction process mentioned in step 5) is further described in the following:

We obtained the road surface area in step 4). However, the pixels in each line may be discontinuous and intermittent due to the disturbances from vehicles and green belt. Direct use of these pixels to derive median brightness value is highly subjected to these interferences. To resolve this issue, we in turn identify the maximum length of the continuous set of pixels Pix(i,j) in $j^{th}$ row, which starts at $(a, j)$ and ends at $(b, j)$ with a length of lengh $(j) = (b-a+1)$; the middle point of Pix $(i, j)$ is $((b+a)/2, j)$; when b+a is an odd number, the operation continues according to the conventional integer rule, namely one of the two pixels in the middle is arbitrarily picked as the midpoint. The coordinates of the midpoint of each line is selected as the center of the road surface measuring band; a road surface measuring band is formed under the conditions set forth by formula (15).

$$\text{len}(\text{Pix}(j)) = \min(\text{Lengh}, \text{lengh}(j)) \quad (15)$$

Where Pix (j) is the set of representative pixels in the $j^{th}$ row of the measuring band with a length of len (Pix (j)); Lengh is a constant threshold value based on image resolution and normally set at 5% to 10% of the horizontal resolution of the image; in this case, the threshold value Lengh is set as 50 based on image resolution of 704*576 with a horizontal resolution of 704. The measuring band and the midpoints are schematically illustrated in FIG. 8. The median brightness value for each line of the measuring band is calculated according to the following formula:

$$B_j = \text{median}(\text{Pix}(j)) \quad (16)$$

After obtaining the brightness-distance curve B, we find the second derivative of curve B to determine the mutation point $v_j$; this result combined with camera calibration, we calculate the extinction coefficient and subsequently arrive at the value of the maximum visibility distance. Brightness B changes gradually with distance; however, two adjacent rows quite often will have a same brightness value because the brightness values are set to range from 0 to 255, which are discrete integer values; furthermore, many confusing second derivative zero points will result because of the interferences from noise points. In order to avoid these false detections, we perform interpolation and filtering on curve B to eliminate confusing second derivative zero points before we look for the first derivative maxima of curve B, i.e. second order mutation points of the brightness function. As illustrated in FIG. 9, the horizontal axis represents the image coordinate system coordinates in the vertical direction; this is the distance between the target point and the camera in the image coordinate system; the blue line represents the first order derivative value of the brightness for each line and the red line represents the filter effect diagram for the first order derivative; the maximum point on the first order derivative is the brightness feature point on the second order derivative and the visibility is calculated according to this.

The process of visibility calculation as mentioned in step 6) is described as follows:

61) The relationship between atmospheric visibility and extinction coefficient

Atmospheric visibility reflects atmospheric transparency index. It is generally defined as the maximum distance one can see and identify a black target object of appropriate size, with the sky on scattered light as background and near the surface of the earth. This definition of visibility varies depending on the human vision. There is apparent difference of image perception ability between human and computer. As shown in FIG. 5, a computer can accurately distinguish the difference between any two levels on a 16-bit gray scale level image, while the human eye can only tell that there is a large difference in luminance level of the object.

According to the definition of CIE, human eye is able to distinguish image pixel of a target object with a contrast ratio greater than 0.05 pixels relative to the background. Computers can only help us detect and measure visibility after we are able to determine the difference in image perception abilities between the human eye and computer.

Koschmieder proposed that light attenuates as it passes through the atmosphere, with the sky as background. Given k as the atmospheric extinction coefficient, d as the distance between a human eye and an object with fixed brightness, and the perceived brightness or radiance of the object as L, the object's intrinsic brightness as $L_0$, and background luminance as $L_f$, the following expression states the relationships between these variables:

$$L = L_0 e^{-kd} + L_f(1 - e^{-kd}) \quad (9)$$

Formula (9) indicates that the brightness of an object consists of two parts: intrinsic brightness of the object $L_0$, which weakens at the rate of $e^{-kd}$; and the background luminance $L_f$, which gradually strengthens at the rate of $(1-e^{-kd})$. As illustrated in FIG. 6, the relationship between the contrast variation, the atmospheric extinction coefficient k, and distance d can be expressed as:

$$C_d = \frac{L - L_f}{L_f} = \frac{L_0 - L_f}{L_f} e^{-kd} = C_0 e^{-kd} \quad (10)$$

In formula (10), $C_d$ is the receiving brightness contrast of the target object and $C_0$ is the intrinsic brightness contrast. The relationship expressed in formula (10) is true when the scattering coefficient is independent of the azimuth angle and there is a uniform illumination along the whole path between the observer, the object, and the horizon sky.

Let $V_{met}$ be the maximum distance of observation by human eyes, i.e. the pixel points with a contrast ratio of 0.05, we have:

$$V_{met} = -\frac{1}{k} \ln\left(\frac{C_d}{C_0}\right) = -\frac{1}{k} \ln(0.05) \approx \frac{3}{k} \quad (11)$$

Equation (11) expresses the relationship between the atmospheric visibility and the extinction coefficient.

62) The solution to visibility based on brightness feature point

We have the second derivative of the image brightness in relation to the image plane vertical coordinate v as:

$$\frac{d^2 L}{dv^2} = k \frac{\lambda(L_0 - L_f)}{(v - v_h)^3} e^{-k \frac{\lambda}{v - v_h}} \left(\frac{k\lambda}{v - v_h} - 2\right) \quad (12)$$

Under the effect of the extinction coefficient k, the image pixel brightness L and its derivative change with distance. As the fog becomes denser, the target object becomes more blurred with the sky as background, and the resulting extreme point value is decreasing. Let the second derivative be 0 and discard the meaningless solution when k=0, we get:

$$k = \frac{2(v_i - v_h)}{\lambda} \quad (13)$$

Where $v_i$ is the inflection point of the second order luminance curve, $v_h$ is the horizon or extinction point, whereby the value of atmospheric visibility distance:

$$V_{met} \approx \frac{3}{k} = \frac{3\lambda}{2(v_i - v_h)} \quad (14)$$

As $v_i$ approaches $v_h$, $V_{met}$ is in a critical state, this is the point of time when one can see the fog appearing; when $v_i$ is greater than $v_h$, it is possible to detect the resulting fog; on the other hand, when $v_i$ is less than $v_h$, we consider it as no fog.

The following is an illustration of how this invention implements the road visibility detection process.

The hardware configuration for this visibility detection experiment is a P4/2.8 GHz PC with a single CPU, 1G of memory, and running SUSE Linux operating system. Video capture comes from Jiangsu Province's Nanjing-Lianyungang Expressway video surveillance images in MPEG-2 format and a resolution of 704×576.

FIG. 10 shows a set of 4 images from the same scene as the visibility gradually changes, each image captured at a 30-min time interval; the "+" in the figure represents the critical visibility value resulted from the contrast algorithm; horizontal position indicates the visibility value obtained by the method of this invention, where V represents visibility value observed by the human eye.

FIG. 11 shows the comparison of the three visibility values detected by this invention, observed by human eye, and derived from contrast algorithm from the scene during the experiment period. The visibility result of this invention is consistent with human eye observation, with an accuracy rate of greater than 96% and a detection error within 10 meters. In comparison to the contrast algorithm, this invention has the advantages of simple operation, strong ability of interference avoidance, and high degree of accuracy.

FIGS. 10 and 11 further show that the detected maximum visible distance is closer to the top of the image as the visibility increases; in most cases, the method of this invention produces consistent results as human eye observation and is in agreement with the results from the contrast algorithm. This method has slight fluctuation within allowable error range. Comparing to the hopping results and higher error rate produced by the contrast algorithm when image noise is relatively large or under masses of fog, the method in this invention can produce relatively better visibility values.

We claim:

1. A method to detect PTZ video image visibility based on luminance features of an image, with the characteristics of
    using PTZ video cameras to obtain road condition video images, to extract the road surface domain of interest (ROI), and to achieve the selected pixel height consistency;
    using region-growing algorithm based on Nagao filter to obtain accurate road surface area, removing interference from the roadbed and vehicles, ensuring consistent illumination of selected image pixels in world coordinates;
    extracting contrast curve reflecting road surface brightness variation within the road surface area, identifying feature points of the brightness curve, and calculating the farthest image pixel distinguishable to human eye through the use of extinction coefficient; and
    calculating the maximum visibility distance in combination with the camera calibration, and determining visibility value,
    comprising the following steps:
    1) collecting real-time road condition video images through existing PTZ video cameras;
    2) determining the conversion relationship between the images and their corresponding world coordinates of the road surface through the camera calibration technology, after processing the video images from the video cameras, and calculating the distance of the road surface [ ] area of the video images and camera;
    3) using Kluge model fit lane division lines to the projections of the video images, through the unknown parameters from randomly solved Hough model, designating the area between the lane division lines as current region of interest (ROI); limiting subsequent image processing to the ROI to ensure the consistency of image pixel height;
    4) using region-growing algorithm, combined with ROI brightness criteria and adaptive Nagao filtering method, extracting road mask area accurately and focusing all subsequent processing on the mask area to reduce the number of calculations and to ensure consistent brightness of the selected pixels within the world coordinates;

calculating the gray scale median value median($P_g$) of the bottom-most line of the ROI, selecting the pixel with brightness of median($P_g$) as seeding point, scanning mask area according to bottom-to-top, left-to-right progressive scan principle, determining scanned target pixel P(i, j) whether it belongs to the road surface area according to the following growth criteria:

41) Brightness balance

P(i, j) and median($P_g$) satisfy $$P(i,j)-\text{median}(P_g) \le \rho n_r \min G_{max}^k$$

(k=−1,0,1)  (6)

In formula (6), ρ is a constant less than 1, $n_r$ is the number of separating rows between P(i, j) and initial seeding point $P_g$, $G_{max}$ refers to the brightness difference between the pixel and its top 3-neighborhood pixels, with top 3-neighborhood pixels referring to the three pixels on top-left, top, and top-right of the pixel; top-left brightness difference is $G_{max}^{-1}$, top brightness difference is $G_{max}^0$, and top-right brightness difference is $G_{max}^1$, among them:

$$G_{max}^{-1} = G_{max}^1 < G_{max}^0 \quad (7)$$

42) Illumination consistency

With image noise filtered using adaptive window width Nagao median filter without diffusing noise point energy, the pixels meeting the balance of pixel brightness are further filtered with adaptive window width Nagao median filter to get the pixel gray scale value Q(i, j) which satisfies:

∃m∈{−1,i,i+1}

$$Q(i,j)-Q(m,j+1) < G_{max}^{i-m} \quad (8)$$

Pixels meeting the continuity and consistency of brightness are added to the road surface domain until the mask area scan is complete, resulted in an accurate road surface area;

5) extracting a brightness feature, including:
using the initial road surface domain with consistent illumination and consistent pixel height obtained in the previous step, coupled with the analysis on the trend of change in road surface pixel luminance caused by atmospheric extinction,
identifying feature point of change, which is also the zero point for the second derivative of the luminance curve;

6) calculating visibility, including:
using the vanishing point coordinates obtained through camera calibration algorithm and the camera parameters, together with the zero point coordinates from the second derivative of luminance curve to determine atmospheric extinction coefficient;
using the Koschmieder Theory then to deduce the relationship between atmospheric extinction coefficient and visibility, thus resulting in the visibility value.

2. The method of claim 1, wherein the PTZ video image visibility detection method based on luminance features of images has a characteristic of camera calibration which is mentioned in step 2):

PTZ video camera image mapping model includes three coordinate systems: road surface world coordinate system ($X_w, Y_w, Z_w$), the camera coordinate system ($X_c, Y_c, Z_c$), and the video image on the image plane coordinates (u,v); with the angle between $Z_c$ and road surface as θ, the distance from camera optical center O to road surface as H, and f as the effective focal length of the lens, the transformation relations between the road coordinate system and the camera coordinate system, the camera coordinate and the image plane are as follows:

$$\begin{pmatrix} X_c \\ Y_c \\ Z_c \\ 1 \end{pmatrix} = \begin{pmatrix} 1 & 0 & 0 & 0 \\ 0 & -\sin\theta & -\cos\theta & H\cos\theta \\ 0 & \cos\theta & -\sin\theta & H\sin\theta \\ 0 & 0 & 0 & 1 \end{pmatrix} \begin{pmatrix} X_w \\ Y_w \\ Z_w \\ 1 \end{pmatrix} \quad (1)$$

$$u = -f\frac{X_c}{Z_c} \quad v = -f\frac{Y_c}{Z_c} \quad (2)$$

With $Y_w = +\infty$ we get the horizon $v_h$, which is the vanishing point in the image plane of the projection:

$$v_h = -f\tan\theta \quad (3)$$

Put this in formula (2) we have:

$$\frac{v-v_h}{f} = \frac{Y_c}{Z_c} + \tan\theta \quad (4)$$

$$Y_c = L - d\sin\theta \quad Z_c = d\cos\theta$$

Accordingly, the distance between the pixels in an image area representing the road surface and the camera optical center $d_c$ can be expressed as:

$$d_c = \begin{cases} \dfrac{\lambda}{(v-v_h)} & v > v_h \\ \infty & v \le v_h \end{cases} \quad \lambda = \frac{Hf}{\cos^2\theta}. \quad (5)$$

3. The method of claim 1, wherein the PTZ video image visibility detection method based on luminance features of images is characterized in step 6) by the relationship between the atmospheric visibility and the extinction coefficient, which is further described as follows:

According to the Koschmieder Equation, let atmospheric extinction coefficient be k, an object of fixed brightness at a distance of d from the observing human eye, with the luminance or radiance value of L, the brightness of the object itself $L_0$, and the background luminance $L_f$ have a relationship as described in the following expression:

$$L = L_0 e^{-kd} + L_f(1-e^{-kd}) \quad (9)$$

Formula (9) indicates that the brightness of an object consists of two parts: intrinsic brightness of the object $L_0$, which weakens at a rate of $e^{-kd}$, and the background luminance $L_f$, which strengthens at a rate of $1-e^{-kd}$, the relationship between the contrast change, the atmospheric extinction coefficient k, and the distance d is expressed as follows:

$$C_d = \frac{L-L_f}{L_f} = \frac{L_0-L_f}{L_f} e^{-kd} = C_0 e^{-kd} \quad (10)$$

In formula (10), $C_d$ is the receiving brightness contrast of the target object, and $C_0$ is the intrinsic brightness contrast; the relationship expressed in formula (10) is true when the scattering coefficient is independent of the azimuth angle and there is a uniform illumination along the whole path between the observer, the object, and the horizon sky, Let $V_{met}$ be the maximum distance of observation by human eyes, i.e. the pixel points with a contrast ratio of 0.05, we have:

$$V_{met} = -\frac{1}{k}\ln\left(\frac{C_d}{C_0}\right) = -\frac{1}{k}\ln(0.05) \approx \frac{3}{k} \quad (11)$$

Equation (11) expresses the relationship between the atmospheric visibility and the extinction coefficient;

The solution process for visibility value based on luminance characteristic is as follows:

Seeking the second derivative of the image brightness curve L in relation to vertical coordinate v of image plane, substituting distance d with equation (5), we have:

$$\frac{d^2L}{dv^2} = k\frac{\lambda(L_0 - L_f)}{(v - v_h)^3}e^{-k\frac{\lambda}{v-v_h}}\left(\frac{k\lambda}{v - v_h} - 2\right) \quad (12)$$

Under the effect of the extinction coefficient k, the image pixel brightness L and its derivative change with distance; as the fog becomes denser, the target object becomes more blurred with the sky as background, and the resulted extreme point value is decreasing; let the second derivative be 0 and discard the meaningless solution when k=0, we get:

$$k = \frac{2(v_i - v_h)}{\lambda} \quad (13)$$

Where $v_i$ is the inflection point of the second order luminance curve, i.e. the second derivative zero point, $v_h$ is the horizon or extinction point, whereby the value of atmospheric visibility distance:

$$V_{met} \approx \frac{3}{k} = \frac{3\lambda}{2(v_i - v_h)} \quad (14)$$

As $v_i$ approaches $v_h$, $V_{met}$ is in a critical state, this is the point of time when one can see the fog appearing; when $v_i$ is greater than $v_h$, it is possible to detect the resulting fog; on the other hand, when $v_i$ is less than $v_h$, we consider it as no fog.

4. The method of claim 1, wherein the PTZ video image visibility detection method based on luminance features of image is characterized in step 5) and further described here. Within the road surface area identified in step 4), we in turn search for the maximum length of the continuous set of pixels Pix(i, j) in $j^{th}$ row, which starts at (a, j) and ends at (b, j) with a length of lengh(j)=(b−a+1); the middle point of Pix(i, j) is ((b+a)/2, j), and the midpoint of each line is the center of road surface measuring band; a road surface measuring band is identified under the condition set forth by formula (15):

$$\text{len}(\text{Pix}(j)) = \min(\text{Lengh}, \text{lengh}(j)) \quad (15)$$

wherein Pix(j) is the set of pixels in $j^{th}$ row of the measuring band, len(Pix(j)) is its length, and Lengh is a constant set threshold; after acquiring the median luminance values in each row of the measuring band, a luminance-distance change curve B is generated; after seeking the second derivative of curve B, the variation feature point $v_i$ is identified which is also the second derivative zero point; to reduce error and get accurate measurements, we interpolate curve B and filter noise to eliminate confusion on the second derivative zero point before we look for the second derivative zero point.

5. The method of claim 3, wherein the PTZ video image visibility detection method based on luminance features of image is characterized in step 5) and further described here. Within the road surface area identified in step 4), we in turn search for the maximum length of the continuous set of pixels Pix(i, j) in $j^{th}$ row, which starts at (a, j) and ends at (b, j) with a length of lengh(j)=(b−a+1); the middle point of Pix(i, j) is ((b+a)/2, j), and the midpoint of each line is the center of road surface measuring band; a road surface measuring region is identified under the condition set forth by formula (15):

$$\text{len}(\text{Pix}(j)) = \min(\text{Lengh}, \text{lengh}(j)) \quad (15)$$

wherein Pix(j) is the set of pixels in $j^{th}$ row of the measuring band, len(Pix(j)) is its length, and Lengh is a constant set threshold; after acquiring the median luminance values in each row of the measuring band, a luminance-distance change curve B is generated; after seeking the second derivative of curve B, the variation feature point $v_i$ is identified which is also the second derivative zero point; to reduce error and get accurate measurements, we interpolate curve B and filter noise to eliminate confusion on the second derivative zero point before we look for the second derivative zero point.

6. The method of claim 2, wherein the PTZ video image visibility detection method based on luminance features of images is characterized in step 6) by the relationship between the atmospheric visibility and the extinction coefficient, which is further described as follows:

According to the Koschmieder Equation, let atmospheric extinction coefficient be k, an object of fixed brightness at a distance of d from the observing human eye, with the luminance or radiance value of L, the brightness of the object itself $L_0$, and the background luminance $L_f$ have a relationship as described in the following expression:

$$L = L_0 e^{-kd} + L_f(1 - e^{-kd}) \quad (9)$$

Formula (9) indicates that the brightness of an object consists of two parts: intrinsic brightness of the object $L_0$, which weakens at a rate of $e^{-kd}$, and the background luminance $L_f$, which strengthens at a rate of $1-e^{-kd}$, the relationship between the contrast change, the atmospheric extinction coefficient k, and the distance d is expressed as follows:

$$C_d = \frac{L - L_f}{L_f} = \frac{L_0 - L_f}{L_f}e^{-kd} = C_0 e^{-kd} \quad (10)$$

In formula (10), $C_d$ is the receiving brightness contrast of the target object, and $C_0$ is the intrinsic brightness contrast; the relationship expressed in formula (10) is true when the scattering coefficient is independent of the azimuth angle and there is a uniform illumination along the whole path between the observer, the object, and the horizon sky.

Let $V_{met}$ be the maximum distance of observation by human eyes, i.e. the pixel points with a contrast ratio of 0.05, we have:

$$V_{met} = -\frac{1}{k}\ln\left(\frac{C_d}{C_0}\right) = -\frac{1}{k}\ln(0.05) \approx \frac{3}{k} \quad (11)$$

Equation (11) expresses the relationship between the atmospheric visibility and the extinction coefficient;

The solution process for visibility value based on luminance characteristic is as follows:

Seeking the second derivative of the image brightness curve L in relation to vertical coordinate v of image plane, substituting distance d with equation (5), we have:

$$\frac{d^2 L}{dv^2} = k \frac{\lambda(L_0 - L_f)}{(v - v_h)^3} e^{-k\frac{\lambda}{v - v_h}} \left( \frac{k\lambda}{v - v_h} - 2 \right) \quad (12)$$

Under the effect of the extinction coefficient k, the image pixel brightness L and its derivative change with distance; as the fog becomes denser, the target object becomes more blurred with the sky as background, and the resulted extreme point value is decreasing; let the second derivative be 0 and discard the meaningless solution when k=0, we get:

$$k = \frac{2(v_i - v_h)}{\lambda} \quad (13)$$

Where $v_i$ is the inflection point of the second order luminance curve, i.e. the second derivative zero point, $v_h$ is the horizon or extinction point, whereby the value of atmospheric visibility distance:

$$V_{met} \approx \frac{3}{k} = \frac{3\lambda}{2(v_i - v_h)} \quad (14)$$

As $v_i$ approaches $v_h$, $V_{met}$ is in a critical state, this is the point of time when one can see the fog appearing; when $v_i$ is greater than $v_h$, it is possible to detect the resulting fog; on the other hand, when $v_i$ is less than $v_h$, we consider it as no fog.

7. The method of claim 2, wherein the PTZ video image visibility detection method based on luminance features of image is characterized in step 5) and further described here. Within the road surface area identified in step 4), we in turn search for the maximum length of the continuous set of pixels Pix(i, j) in $j^{th}$ row, which starts at (a, j) and ends at (b, j) with a length of lengh(j)=(b−a+1); the middle point of Pix(i, j) is ((b+a)/2, j), and the midpoint of each line is the center of road surface measuring band; a road surface measuring band is identified under the condition set forth by formula (15):

$$\text{len}(Pix(j)) = \min(\text{Lengh}, \text{lengh}(j)) \quad (15)$$

wherein Pix(j) is the set of pixels in $j^{th}$ row of the measuring band, len(Pix(j)) is its length, and Lengh is a constant set threshold; after acquiring the median luminance values in each row of the measuring band, a luminance-distance change curve B is generated; after seeking the second derivative of curve B, the variation feature point $v_i$ is identified which is also the second derivative zero point; to reduce error and get accurate measurements, we interpolate curve B and filter noise to eliminate confusion on the second derivative zero point before we look for the second derivative zero point.

* * * * *